United States Patent
Urick et al.

(12)

(10) Patent No.: US 6,416,457 B1
(45) Date of Patent: Jul. 9, 2002

(54) SYSTEM AND METHOD FOR INTRAVASCULAR IONIZING TANDEM RADIATION THERAPY

(75) Inventors: Michael J. Urick, Rogers, MN (US); Vitali E. Verin; Youri G. Popowski, both of Geneva (CH)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/522,122

(22) Filed: Mar. 9, 2000

(51) Int. Cl.[7] .............................................. A61N 5/00
(52) U.S. Cl. .................................................... 600/3
(58) Field of Search .......................................... 600/1–8

(56) References Cited

U.S. PATENT DOCUMENTS

| | | | |
|---|---|---|---|
| 2,546,761 A | 3/1951 | Loftus | 128/1.2 |
| 2,862,108 A | 11/1958 | Meilink | 250/106 |
| 2,955,208 A | 10/1960 | Stevens | 250/108 |
| 3,060,924 A | 10/1962 | Rush | 128/1.2 |
| 3,147,383 A | 9/1964 | Prest | 250/108 |
| 3,324,847 A | 6/1967 | Zoumboulis | 128/1.2 |
| 3,505,991 A | 4/1970 | Hellerstein et al. | 128/1.1 |
| 3,643,096 A | 2/1972 | Jeffries, Jr. et al. | 250/108 R |
| 3,669,093 A | 6/1972 | Sauerwein et al. | 128/1.1 |
| 3,674,006 A | 7/1972 | Holmer | 128/1.2 |
| 3,750,653 A | 8/1973 | Simon | 128/1.2 |
| 3,811,426 A | 5/1974 | Culver et al. | 128/1.2 |
| 3,861,380 A | 1/1975 | Chassagne et al. | 128/1.2 |
| 3,866,050 A | 2/1975 | Whitfield | 250/497 |
| 3,927,325 A | 12/1975 | Hungate et al. | 250/435 |
| 4,096,862 A | 6/1978 | DeLuca | 128/348 |
| 4,220,864 A | 9/1980 | Sauerwein et al. | 250/497 |
| 4,225,790 A | 9/1980 | Parsons, Jr. et al. | 250/497 |

(List continued on next page.)

FOREIGN PATENT DOCUMENTS

| | | |
|---|---|---|
| CA | 2166915 A | 8/1996 |
| DE | G 91 02 312.2 | 8/1992 |

(List continued on next page.)

OTHER PUBLICATIONS

Tjho–Heslinga et al., "Results of ruthenium irradiation of uveal melanona", *Radiothereapy Oncology*, vol. 29, pp. 33–38, 1993.

Lommatzwsch et al., "Radiation effects on the optic nerve observed after brachytherapy of choroidal melanomas with 106Ru/106Rh plaques", *Graefe's Arch. Clin. Exp. Ophthalmology* vol. 232, pp. 482–487, 1994.

*Radiotherapy of Intraoculare and Orbital Tumors*, Springer–Verlak publishers, Berlin Heidelberg and New York, copyright 1993, pp. 23–30 and 363–367.

Fackelmann, "Harbinger of a Heart Attack", *Science News*, vol. 151, Jun. 14, 1997, pp. 374–375.

Raloff, "Nuclear Medicine Gets Friendlier—Experimental Therapies Seek to Poison Just the Disease", *Science News*, vol. 152, Jul. 19, 1997, pp. 40–41.

Sutherland, "Managing Cancer Through Synergy", *Administrative Radiology Journal*, Nov. 1996, pp. 21–27.

*Primary Examiner*—John P. Lacyk
(74) *Attorney, Agent, or Firm*—Crompton, Seager & Tufte, LLC

(57) ABSTRACT

A system for intravascular ionizing radiation therapy including a radiation device and a guide wire having radiopaque markers to facilitate precise repositioning of the radiation source along the length of the treatment site. The radiopaque markers are separated by a distance L, which corresponds to the distance between the 50% dose points in the dose fall-off regions. This produces partial dose overlap when the radioactive source is positioned in tandem adjacent each radiopaque marker. Preferably, only the dose fall-off regions overlap thereby providing more uniform and complete radiation exposure along the length of the treatment site.

17 Claims, 4 Drawing Sheets

U.S. PATENT DOCUMENTS

| | | | |
|---|---|---|---|
| 4,244,357 A | 1/1981 | Morrison | 128/1.2 |
| 4,281,252 A | 7/1981 | Parsons, Jr. et al. | 250/497 |
| 4,314,157 A | 2/1982 | Gaines | 250/497 |
| 4,364,376 A | 12/1982 | Bigham | 128/1.1 |
| 4,584,991 A | 4/1986 | Tokita et al. | 128/1.1 |
| 4,588,395 A | 5/1986 | Lemelson | 604/59 |
| 4,631,415 A | 12/1986 | Sauerwein et al. | 250/497.1 |
| 4,702,228 A | 10/1987 | Russell, Jr. et al. | 128/1.2 |
| 4,706,652 A | 11/1987 | Horowitz | 128/1.2 |
| 4,763,642 A | 8/1988 | Horowitz | 128/1.2 |
| 4,763,671 A | 8/1988 | Goffinet | 128/786 |
| 4,782,834 A | 11/1988 | Maguire et al. | 128/344 |
| 4,784,116 A | 11/1988 | Russell, Jr. et al. | 128/1.2 |
| 4,815,449 A | 3/1989 | Horowitz | 600/7 |
| 4,819,618 A | 4/1989 | Liprie | 600/7 |
| 4,851,694 A | 7/1989 | Rague et al. | 250/497.1 |
| 4,861,520 A | 8/1989 | van't Hooft et al. | 252/644 |
| 4,881,937 A | 11/1989 | van't Hooft et al. | 600/3 |
| 4,897,076 A | 1/1990 | Puthawala et al. | 600/7 |
| 4,936,823 A | 6/1990 | Colvin et al. | 600/7 |
| 4,963,128 A | 10/1990 | Daniel et al. | 600/7 |
| 4,969,863 A | 11/1990 | van't Hooft et al. | 600/3 |
| 4,976,266 A | 12/1990 | Huffman et al. | 128/659 |
| 4,976,680 A | 12/1990 | Hayman et al. | 600/7 |
| 4,976,690 A | 12/1990 | Solar et al. | 604/96 |
| 5,030,194 A | 7/1991 | Van't Hooft | 600/3 |
| 5,032,113 A | 7/1991 | Burns | 604/96 |
| 5,059,166 A | 10/1991 | Fischell et al. | 600/3 |
| 5,084,001 A | 1/1992 | Van't Hooft et al. | 600/3 |
| 5,084,002 A | 1/1992 | Liprie | 600/7 |
| 5,092,834 A | 3/1992 | Bradshaw et al. | 600/7 |
| 5,103,395 A | 4/1992 | Spako et al. | 364/413.26 |
| 5,106,360 A | 4/1992 | Ishiwara et al. | 600/2 |
| 5,120,973 A | 6/1992 | Rohe et al. | 250/497.1 |
| 5,139,473 A | 8/1992 | Bradshaw et al. | 600/3 |
| 5,141,487 A | 8/1992 | Liprie | 600/7 |
| 5,147,282 A | 9/1992 | Kan | 600/1 |
| 5,163,896 A | 11/1992 | Suthanthiran et al. | 600/8 |
| 5,176,617 A | 1/1993 | Fischell et al. | 600/3 |
| 5,183,455 A | 2/1993 | Hayman et al. | 600/7 |
| 5,199,939 A | 4/1993 | Dake et al. | 600/3 |
| 5,209,730 A | 5/1993 | Sullivan | 604/96 |
| 5,213,561 A | 5/1993 | Weinstein et al. | 600/7 |
| 5,267,960 A | 12/1993 | Hayman et al. | 604/106 |
| 5,282,781 A | 2/1994 | Liprie | 600/3 |
| 5,302,168 A | 4/1994 | Hess | 600/3 |
| 5,344,383 A | 9/1994 | Liping | 600/3 |
| 5,354,257 A | 10/1994 | Roubin et al. | 600/7 |
| 5,370,685 A | 12/1994 | Stevens | 623/2 |
| 5,391,139 A | 2/1995 | Edmundson | 600/7 |
| 5,395,300 A | 3/1995 | Liprie | 600/3 |
| 5,405,309 A | 4/1995 | Carden, Jr. | 600/3 |
| 5,409,015 A | 4/1995 | Palermo | 128/772 |
| 5,411,466 A | 5/1995 | Hess | 600/3 |
| 5,425,720 A | 6/1995 | Rogalsky et al. | 604/198 |
| 5,429,582 A | 7/1995 | Williams | 600/2 |
| 5,484,384 A | 1/1996 | Fearnot | 600/3 |
| 5,498,227 A | 3/1996 | Mawad | 600/3 |
| 5,503,613 A | 4/1996 | Weinberger | 600/3 |
| 5,503,614 A | 4/1996 | Liprie | 600/7 |
| 5,532,122 A | 7/1996 | Drukier | 435/5 |
| 5,538,494 A | 7/1996 | Matsuda | 600/1 |
| 5,540,659 A | 7/1996 | Teirstein | 604/104 |
| 5,556,389 A | 9/1996 | Liprie | 604/264 |
| 5,575,749 A | 11/1996 | Liprie | 600/3 |
| 5,605,530 A | 2/1997 | Fischell et al. | 600/3 |
| 5,611,767 A | 3/1997 | Williams | 600/2 |
| 5,616,114 A | 4/1997 | Thornton et al. | 600/3 |
| 5,618,266 A | 4/1997 | Liprie | 604/21 |
| 5,624,372 A | 4/1997 | Liprie | 600/3 |
| 5,643,171 A | 7/1997 | Bradshaw et al. | 600/1 |
| 5,649,924 A | 7/1997 | Everett et al. | 606/15 |
| 5,653,683 A | 8/1997 | D'Andrea | 604/21 |
| 5,662,580 A | 9/1997 | Bradshaw et al. | 600/3 |
| 5,674,177 A | 10/1997 | Hehrlein et al. | 600/3 |
| 5,683,345 A | 11/1997 | Waksman et al. | 600/3 |
| 5,688,220 A | 11/1997 | Verin et al. | 600/1 |
| 5,707,332 A | 1/1998 | Weinberger | 600/3 |
| 5,713,828 A | 2/1998 | Coniglione | 600/7 |
| 5,720,717 A | 2/1998 | D'Andrea | 604/21 |
| 5,722,984 A | 3/1998 | Fischell et al. | 606/198 |
| 5,728,042 A | 3/1998 | Schwager | 600/3 |
| 5,730,698 A | 3/1998 | Fischell et al. | 600/3 |
| 5,782,740 A | 7/1998 | Schneiderman | 600/1 |
| 5,782,742 A | 7/1998 | Crocker et al. | 600/3 |
| 5,795,286 A | 8/1998 | Fischell et al. | 600/3 |
| 5,800,333 A | 9/1998 | Liprie | 600/3 |
| 5,803,895 A | 9/1998 | Kronholz et al. | 600/3 |
| 5,807,231 A | 9/1998 | Liprie | 600/3 |
| 5,816,259 A | 10/1998 | Rose | 128/898 |
| 5,816,999 A | 10/1998 | Bischoff et al. | 600/3 |
| 5,820,553 A | 10/1998 | Hughes | 600/426 |
| 5,833,593 A | 11/1998 | Liprie | 600/3 |
| 5,840,008 A | 11/1998 | Klein et al. | 600/3 |
| 5,840,009 A | 11/1998 | Fischell et al. | 600/3 |
| 5,840,064 A | 11/1998 | Liprie | 604/96 |
| 5,843,163 A | 12/1998 | Wall | 623/1 |
| 5,851,171 A | 12/1998 | Gasson | 600/3 |
| 5,851,172 A | 12/1998 | Bueche et al. | 600/7 |
| 5,855,546 A | 1/1999 | Hastings et al. | 600/3 |
| 5,857,956 A | 1/1999 | Liprie | 600/7 |
| 5,863,284 A | 1/1999 | Klein | 600/3 |
| 5,863,285 A | 1/1999 | Coletti | 600/3 |
| 5,865,720 A | 2/1999 | Hastings et al. | 600/3 |
| 5,871,436 A | 2/1999 | Eury | 600/3 |
| 5,871,437 A | 2/1999 | Alt | 600/3 |
| 5,873,811 A | 2/1999 | Wang et al. | 600/5 |
| 5,879,282 A | 3/1999 | Fischell et al. | 600/3 |
| 5,882,290 A | 3/1999 | Kume | 600/3 |
| 5,882,291 A | 3/1999 | Bradshaw et al. | 600/3 |
| 5,891,091 A | 4/1999 | Teirstein | 604/104 |
| 5,897,573 A | 4/1999 | Rosenthal et al. | 606/224 |
| 5,899,882 A | 5/1999 | Waksman et al. | 604/96 |
| 5,906,573 A | 5/1999 | Aretz | 600/3 |
| 5,910,101 A | 6/1999 | Andrews et al. | 600/3 |
| 5,910,102 A | 6/1999 | Hastings | 600/3 |
| 5,913,813 A | 6/1999 | Williams et al. | 600/3 |
| 5,916,143 A | 6/1999 | Apple et al. | 600/3 |
| 5,919,126 A | 7/1999 | Armini | 600/3 |
| 5,924,973 A | 7/1999 | Weinberger | 600/3 |
| 5,924,974 A | 7/1999 | Loffler | 600/3 |
| 5,925,353 A | 7/1999 | Mosseri | 424/178.1 |
| 5,938,582 A | 8/1999 | Ciamacco, Jr. et al. | 600/3 |
| 5,947,889 A | 9/1999 | Hehrlein | 600/3 |
| 5,947,924 A | 9/1999 | Liprie | 604/96 |
| 5,947,958 A | 9/1999 | Woodard et al. | 606/1.5 |
| 5,957,829 A | 9/1999 | Thornton | 600/3 |
| 5,961,439 A | 10/1999 | Chernomorsky et al. | 600/4 |
| 5,967,966 A | 10/1999 | Kronholz et al. | 600/3 |
| 5,971,909 A | 10/1999 | Bradshaw et al. | 600/3 |
| 5,976,106 A | 11/1999 | Verin et al. | 604/96 |
| 5,997,462 A | 12/1999 | Loffler | 600/3 |
| 5,997,463 A | 12/1999 | Cutrer | 600/8 |
| 6,010,445 A | 1/2000 | Armini et al. | 600/3 |
| 6,013,019 A | 1/2000 | Fischell et al. | 600/3 |
| 6,013,020 A | 1/2000 | Meloul et al. | 600/7 |
| 6,019,718 A | 2/2000 | Hektner | 600/3 |
| 6,024,690 A | 2/2000 | Lee et al. | 600/3 |
| 6,030,333 A | 2/2000 | Sioshansi et al. | 600/3 |

| | | | | | | |
|---|---|---|---|---|---|---|
| 6,033,357 A | 3/2000 | Ciezki et al. ................... 600/3 | | EP | 0 754 473 A2 | 1/1997 |
| 6,048,300 A | 4/2000 | Thornton et al. .............. 600/7 | | EP | 0 593 136 B1 | 3/1997 |
| 6,050,930 A | 4/2000 | Teirstein ........................ 600/3 | | EP | 0 771 572 | 5/1997 |
| 6,053,858 A | 4/2000 | Bueche et al. .................. 600/3 | | EP | 0 778 051 A1 | 6/1997 |
| 6,059,713 A | 5/2000 | Urick et al. .................... 600/3 | | EP | 0 801 961 A2 | 10/1997 |
| 6,059,752 A | 5/2000 | Segal ......................... 604/107 | | EP | 0810004 | 12/1997 |
| 6,059,812 A | 5/2000 | Clerc et al. .................. 606/198 | | EP | 0 813 894 A2 | 12/1997 |
| 6,090,035 A | 7/2000 | Campbell et al. | | EP | 0 629 380 B1 | 7/1998 |
| 6,099,455 A | 8/2000 | Columbo et al. | | EP | 0 853 957 | 7/1998 |
| 6,106,454 A | 8/2000 | Berg et al. | | EP | 0865803 | 9/1998 |
| 6,110,097 A | 8/2000 | Hastings et al. | | EP | 0904798 | 3/1999 |
| 6,117,065 A | 9/2000 | Hastings et al. | | EP | 0904799 | 3/1999 |
| 6,142,926 A | 11/2000 | Schneiderman | | JP | 1071210 | 3/1998 |
| 6,146,322 A | 11/2000 | Papirov et al. | | JP | 2000014810 | 1/2000 |
| 6,149,574 A | 11/2000 | Trauthen et al. | | JP | 2000024001 | 1/2000 |
| 6,149,575 A | 11/2000 | Leonhardt | | WO | WO 86/03124 | 6/1986 |
| 6,152,869 A | 11/2000 | Park et al. | | WO | WO 93/04735 | 3/1993 |
| 6,162,165 A | 12/2000 | Apple et al. | | WO | WO 94/25106 | 11/1994 |
| 6,179,768 B1 | 1/2001 | Loffler et al. | | WO | WO 94/26205 | 11/1994 |
| 6,200,256 B1 | 3/2001 | Weinberger | | WO | WO 95/07732 | 3/1995 |
| 6,200,257 B1 | 3/2001 | Winkler | | WO | WO 95/19807 | 7/1995 |
| 6,200,307 B1 | 3/2001 | Kasinkas et al. | | WO | WO 96/06654 | 3/1996 |
| 6,203,485 B1 | 3/2001 | Urick | | WO | WO 96/10436 | 4/1996 |
| 6,213,976 B1 | 4/2001 | Trerotola | | WO | WO 96/13303 | 5/1996 |
| 6,217,503 B1 | 4/2001 | Weinberger et al. | | WO | WO 96/14898 | 5/1996 |
| 6,224,535 B1 | 5/2001 | Chiu et al. | | WO | WO 96/17654 | 6/1996 |
| 6,224,536 B1 | 5/2001 | Pike | | WO | WO 96/22121 | 7/1996 |
| 6,231,494 B1 | 5/2001 | Verin et al. | | WO | WO 96/29943 | 10/1996 |
| 6,231,495 B1 | 5/2001 | Denk | | WO | WO 96/40352 | 12/1996 |
| 6,231,719 B1 | 5/2001 | Garvey et al. | | WO | WO 97/07740 | 3/1997 |
| 6,234,951 B1 | 5/2001 | Hastings | | WO | WO 97/09937 | 3/1997 |
| 6,234,952 B1 | 5/2001 | Lipric | | WO | WO 97/17029 | 5/1997 |
| 6,238,332 B1 | 5/2001 | Kanesaka | | WO | WO 97/18012 | 5/1997 |
| 6,241,719 B1 | 6/2001 | Wallace et al. | | WO | WO 97/19706 | 6/1997 |
| 6,248,057 B1 | 6/2001 | Mavity et al. | | WO | WO 97/25102 | 7/1997 |
| 6,251,059 B1 | 6/2001 | Apple et al. | | WO | WO 97/25103 | 7/1997 |
| 6,254,552 B1 | 7/2001 | Lewis et al. | | WO | WO 97/40889 | 11/1997 |
| 6,258,019 B1 | 7/2001 | Verin et al. | | WO | WO 98/01183 | 1/1998 |
| 6,261,219 B1 | 7/2001 | Meloul et al. | | WO | WO 98/01184 | 1/1998 |
| 6,264,579 B1 | 7/2001 | Odai et al. | | WO | WO 98/01185 | 1/1998 |
| 6,264,595 B1 | 7/2001 | Delfino et al. | | WO | WO 98/01186 | 1/1998 |
| 6,264,596 B1 | 7/2001 | Weadock | | WO | WO 98/11936 | 3/1998 |
| 6,264,598 B1 | 7/2001 | Armini | | WO | WO 98/16151 | 4/1998 |
| 6,267,717 B1 | 7/2001 | Stoll et al. | | WO | WO 98/20935 | 5/1998 |
| 6,267,775 B1 | 7/2001 | Clerc et al. | | WO | WO 98/25674 | 6/1998 |
| 6,283,910 B1 | 9/2001 | Bradshaw et al. | | WO | WO 98/29049 | 7/1998 |
| 6,283,911 B1 | 9/2001 | Keren | | WO | WO 98/30273 | 7/1998 |
| 6,287,249 B1 | 9/2001 | Tam et al. | | WO | WO 98/34681 | 8/1998 |
| 6,296,603 B1 | 10/2001 | Turnlund et al. | | WO | WO 98/36788 | 8/1998 |
| 6,302,839 B1 | 10/2001 | Chernomorsky et al. | | WO | WO 98/36790 | 8/1998 |
| 6,293,899 B1 | 11/2001 | Sioshansi et al. | | WO | WO 98/36796 | 8/1998 |
| | | | | WO | WO 98/39052 | 9/1998 |
| FOREIGN PATENT DOCUMENTS | | | | WO | WO 98/39062 | 9/1998 |
| DE | 195 26 680 A1 | 1/1997 | | WO | WO 98/39063 | 9/1998 |
| DE | 197 54 870 A1 | 8/1998 | | WO | WO 98/40032 | 9/1998 |
| DE | 197 24 223 C1 | 12/1998 | | WO | WO 98/46309 | 10/1998 |
| DE | 197 24 233 C1 | 12/1998 | | WO | WO 98/55179 | 12/1998 |
| DE | 197 58 234 | 7/1999 | | WO | WO 98/57706 | 12/1998 |
| DE | 198 07 727 | 7/1999 | | WO | WO 99/01179 | 1/1999 |
| DE | 198 25 563 | 12/1999 | | WO | WO 99/02219 | 1/1999 |
| DE | 198 25 999 | 12/1999 | | WO | WO 99/04706 | 2/1999 |
| DE | 198 26 000 | 12/1999 | | WO | WO 99/04856 | 2/1999 |
| DE | 198 29 444 | 1/2000 | | WO | WO 99/10045 | 3/1999 |
| DE | 198 29 447 | 1/2000 | | WO | WO 99/21615 | 5/1999 |
| EP | 0 514 913 A2 | 11/1992 | | WO | WO 99/21616 | 5/1999 |
| EP | 0 633 041 A1 | 1/1995 | | WO | WO 99/22774 | 5/1999 |
| EP | 0 686 342 A1 | 12/1995 | | WO | WO 99/22775 | 5/1999 |
| EP | 0 688 580 A1 | 12/1995 | | WO | WO 99/22812 | 5/1999 |
| EP | 0 696 906 B1 | 2/1996 | | WO | WO 99/22815 | 5/1999 |
| EP | 0 749 764 A1 | 12/1996 | | WO | WO 99/24116 | 5/1999 |
| EP | 0 754 472 A2 | 1/1997 | | WO | WO 99/24117 | 5/1999 |

| | | | | | | |
|---|---|---|---|---|---|---|
| WO | WO 99/29354 | 6/1999 | | WO | WO 0003292 | 1/2000 |
| WO | WO 99/29370 | 6/1999 | | WO | WO 0004838 | 2/2000 |
| WO | WO 99/29371 | 6/1999 | | WO | WO 0004953 | 2/2000 |
| WO | WO 99/30779 | 6/1999 | | WO | WO 0009212 | 2/2000 |
| WO | WO 99/34969 | 7/1999 | | WO | WO 0029501 | 5/2000 |
| WO | WO 99/36121 | 7/1999 | | WO | WO 00/32271 | 6/2000 |
| WO | WO 99/39628 | 8/1999 | | WO | WO 00/45627 | 8/2000 |
| WO | WO 99/40962 | 8/1999 | | WO | WO 00/56249 | 9/2000 |
| WO | WO 99/40970 | 8/1999 | | WO | WO 00/69503 | 11/2000 |
| WO | WO 99/40971 | 8/1999 | | WO | WO 00/74778 | 12/2000 |
| WO | WO 99/40972 | 8/1999 | | WO | WO 00/76557 | 12/2000 |
| WO | WO 99/40973 | 8/1999 | | WO | WO 01/14011 A1 | 3/2001 |
| WO | WO 99/40974 | 8/1999 | | WO | WO 01/14617 A1 | 3/2001 |
| WO | WO 99/42162 | 8/1999 | | WO | WO 01/21106 A1 | 3/2001 |
| WO | WO 99/42163 | 8/1999 | | WO | WO 01/21245 A1 | 3/2001 |
| WO | WO 99/42177 | 8/1999 | | WO | WO 01/21245 | 3/2001 |
| WO | WO 99/44686 | 9/1999 | | WO | WO 01/21248 A1 | 3/2001 |
| WO | WO 99/44687 | 9/1999 | | WO | WO 01/26734 A1 | 4/2001 |
| WO | WO 99/49935 | 10/1999 | | WO | WO 01/47602 A1 | 7/2001 |
| WO | WO 99/56825 | 11/1999 | | WO | WO 01/54764 A2 | 8/2001 |
| WO | WO 99/56828 | 11/1999 | | WO | WO 01/60443 A1 | 8/2001 |
| WO | WO 99/61107 | 12/1999 | | WO | WO 01/62331 A1 | 8/2001 |
| WO | WO 99/62598 | 12/1999 | | WO | WO 01/64123 A1 | 9/2001 |
| WO | WO 99/66979 | 12/1999 | | WO | WO 01/66188 A1 | 9/2001 |

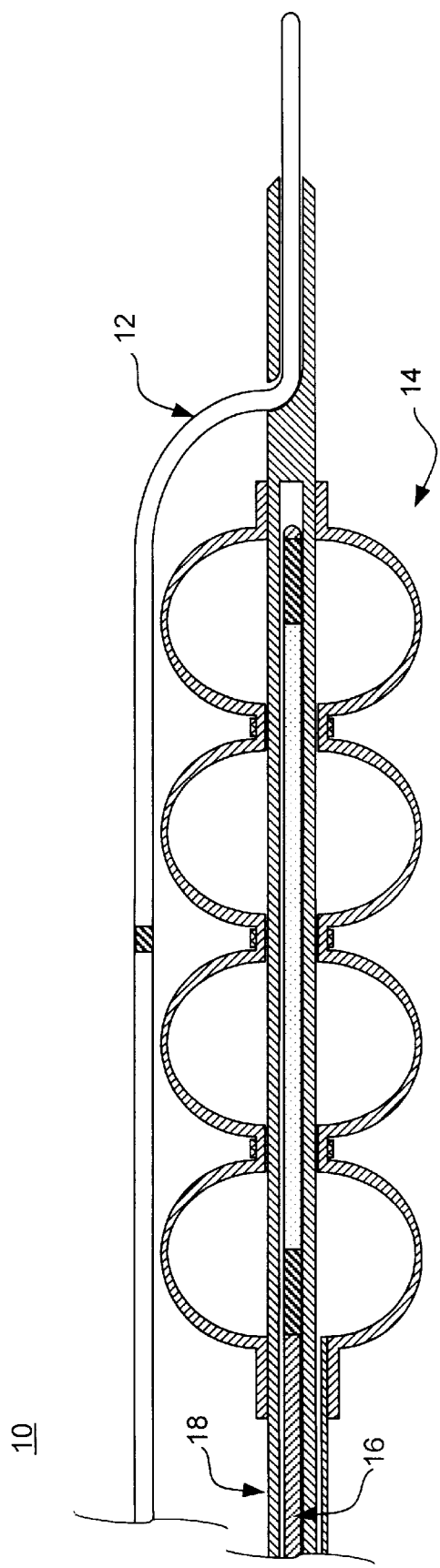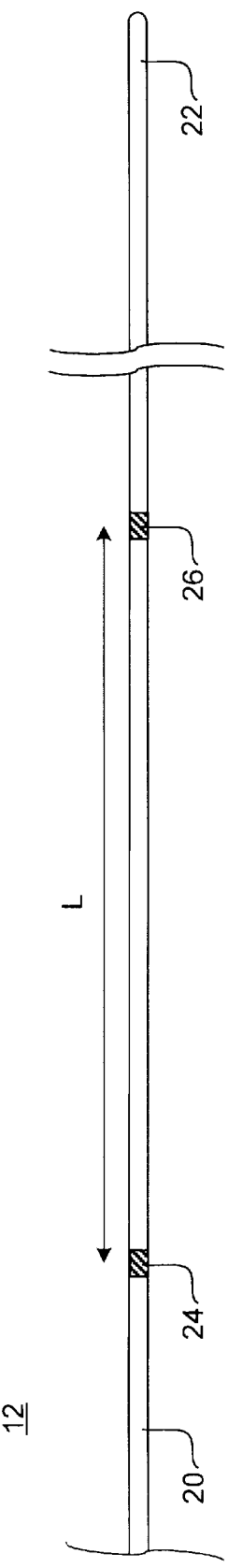

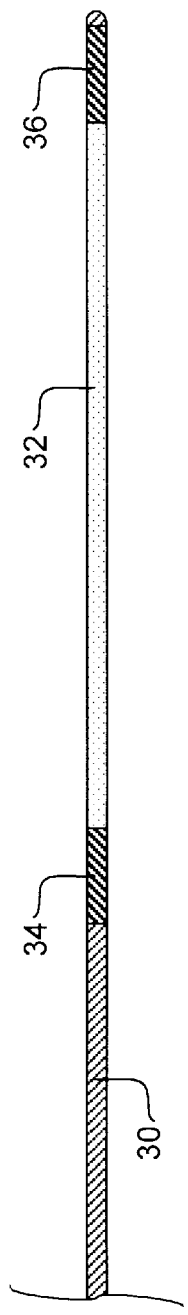
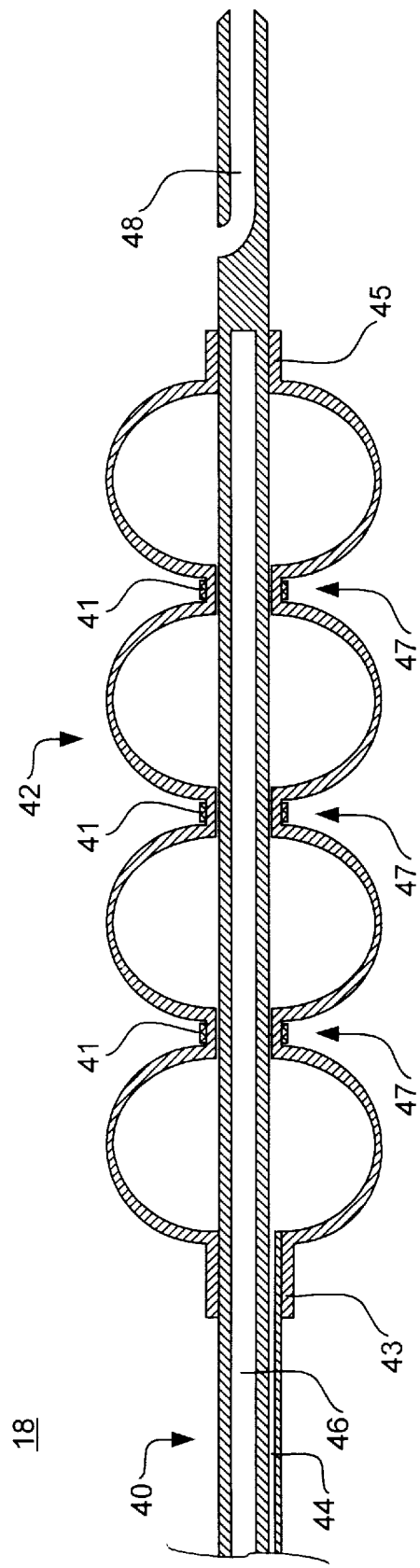
FIG. 3
FIG. 4

SYSTEM AND METHOD FOR INTRAVASCULAR IONIZING TANDEM RADIATION THERAPY

FIELD OF THE INVENTION

The present invention generally relates to medical devices. More specifically, the present invention relates to medical devices suitable for intravascular ionizing radiation therapy.

BACKGROUND OF THE INVENTION

Intravascular ionizing radiation therapy is being used increasingly to treat vascular disease. For example, the administration of ionizing radiation has been proposed as both a primary and a secondary therapy for treating vascular stenosis (a vascular restriction or narrowing). Clinical studies have shown that ionizing radiation may be used to inhibit or prevent restenosis after percutaneous transluminal angioplasty (PTA). In coronary applications, such vascular restrictions may range in length from a few millimeters to several centimeters, depending on the extent and nature of the disease, in addition to the size and type of vessel affected.

Typically, physicians evaluate the size and nature of the vascular restriction in order to determine the appropriate treatment parameters (e.g., radiation source length, dose, ect.). Radiation devices commonly utilize a fixed-length ionizing radiation source, and only a limited number of different lengths are available. In some instances, the physician is not able to select a source length that matches the length of the treatment site. In this situation, the physician may elect to use a relatively short radiation source and reposition the source in tandem along the length of the treatment site until the entire site has been exposed to the desired amount of radiation.

However, unless the radiation source is precisely repositioned, various areas of the treatment site will inevitably receive more or less radiation exposure than other areas of the treatment site. Precise repositioning of the radiation source is difficult, if not impossible, due to image foreshortening, even when anatomical landmarks are used as reference points. Thus, there is a need for a more precise method of repositioning the radiation source along the length of the treatment site.

SUMMARY OF THE INVENTION

The present invention overcomes these disadvantages by providing a system for intravascular ionizing radiation therapy including a radiation device and a guide wire, wherein the guide wire includes radiopaque markers that facilitate precise repositioning of the radiation device. The radiopaque markers are separated by a distance L, which is equal to the distance between points in the dose fall-off regions (edge effects) corresponding to 50% of the nominal dose. This produces partial dose overlap when the radioactive source is sequentially positioned adjacent each radiopaque marker. Preferably, only the dose fall off regions (edge effects) overlap thereby providing more uniform and complete radiation exposure along the length of the treatment site.

The radiation device may include a centering catheter and a source wire, wherein the source wire is insertable into the centering catheter. The radioactive source is disposed adjacent the distal end of the source wire. The centering catheter preferably includes a guide wire lumen with the guide wire slidably disposed therein. The centering catheter and/or the source wire may include radiopaque markers for alignment with the radiopaque markers on the guide wire.

The radiation source may be a line source having a dosimetry or dose distribution with a nominal dose, a proximal dose fall-off and a distal dose fall-off. The distance L is preferably about equal to the distance between a point in the proximal dose fall-off and a point in the distal dose fall-off. The proximal and distal points preferably correspond to points on the dose distribution equal to half of the nominal dose such that the total dose at the overlap is approximately equal to the nominal dose.

The present invention also provides a method of administering ionizing radiation at a treatment site within a patient's vasculature. The method includes the steps of: providing a radiation device and a guide wire substantially as described above; navigating the guide wire through the vasculature of the patient until the markers on the guide wire are disposed adjacent the treatment site; inserting the radiation device into the vasculature of the patient over or adjacent to the guide wire; positioning the radioactive source adjacent a marker on the guide wire; and repositioning (in the proximal or distal direction) the radioactive source adjacent the neighboring marker on the guide wire such that slight dose overlap is created thereby providing more uniform and complete radiation exposure along the length of the treatment site.

BRIEF DESCRIPTION OF THE DRAWINGS

FIG. 1 is a partially cross-sectioned side view of a system for intravascular ionizing radiation therapy in accordance with the present invention;

FIG. 2 is a side view of the guide wire used in the system illustrated in FIG. 1;

FIG. 3 is a cross-sectional side view of the source wire used in the system illustrated in FIG. 1;

FIG. 4 is a cross-sectional side view of the centering catheter used in the system illustrated in FIG. 1;

DETAILED DESCRIPTION OF THE INVENTION

Figure 5A:
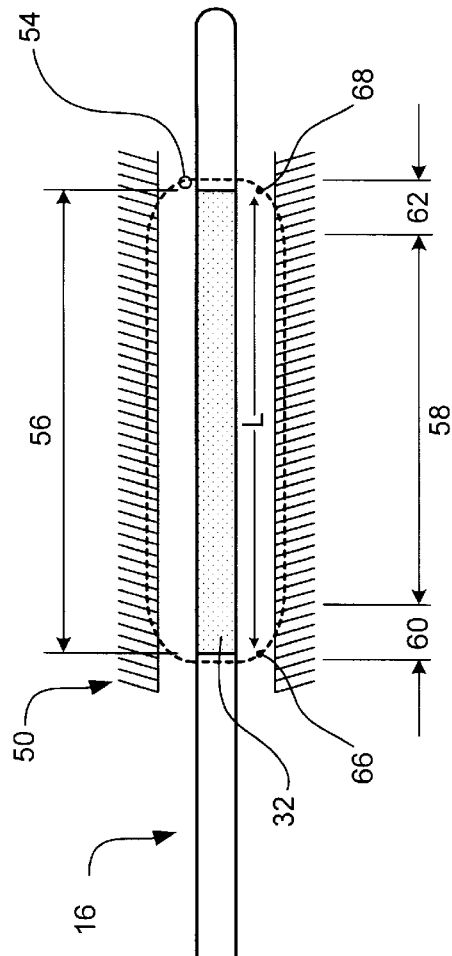
FIGS. 5A and 5B are side views of the radiation source wire disposed in the vasculature illustrating the dose overlap aspect of the present invention.

The following detailed description should be read with reference to the drawings in which similar elements in different drawings are numbered the same. The drawings, which are merely schematic and not necessarily to scale, depict illustrative embodiments and are not intended to limit the scope of the invention.

Refer now to FIG. 1 which illustrates a system 10 for intravascular ionizing radiation therapy in accordance with the present invention. System 10 includes two primary components, namely a guide wire 12 and a radiation device 14. Radiation device 14 may include two separate components, namely a source wire 16 and a centering catheter 18 as shown. However, radiation device 14 may comprise any suitable intravascular device or combination of intravascular devices having a radioactive portion disposed adjacent the distal end thereof. For purposes of illustration only, the radiation device 14 is shown as a source wire 16 and a centering catheter 18. More detailed descriptions of the guide wire 12, the source wire 16, and the centering catheter 18 are provided with reference to FIGS. 2, 3 and 4, respectively.

Refer now to FIG. 2 which illustrates the guide wire 12 utilized in the system 10 illustrated in FIG. 1. With the exception of the placement and use of the radiopaque markers 24 and 26, the guide wire 12 may have a conventional design incorporating an elongate shaft 20 and an atraumatic distal tip 22. A pair of radiopaque markers 24 and 26 are disposed adjacent the distal portion of the guide wire 12. Radiopaque markers 24 and 26 may comprise conventional radiopaque marker designs such as coils or bands formed of radiopaque material and disposed about the elongate shaft 20.

The proximal radiopaque marker 24 is separated by a distance L from the distal radiopaque marker 26. The distance L is selected to provide partial dose overlap as will be discussed in greater detail with reference to FIGS. 5A and 5B. Although guide wire 12 is shown as having only two radiopaque markers 24 and 26, two or more radiopaque markers may be utilized, depending on the length of the treatment site and the length of the radioactive source as will be appreciated from the discussion with reference to FIGS. 6A and 6B.

Refer now to FIG. 3 which illustrates the radiation source wire 16 utilized in the system 10 illustrated in FIG. 1. Elongate source wire 16 includes two primary components, namely an elongate shaft 30 and a distally disposed radioactive source 32. Radioactive source 32 may approximate a line source as illustrated. The radiation source 32 includes a radioisotope emitting ionizing radiation such as beta or gamma radiation. Preferably, the radioactive source 32 comprises a radiation emitting isotope such as Sr/Y-90, P-32, Y-90, Ce/Pr-144, Ru/Rh-106, W/Re-188, Ir-192, I-125, or Pd-103. Radiopaque markers 34 and 36 may be disposed on either side of the radioactive source 32 to facilitate intravascular placement utilizing x-ray fluoroscopy. Elongate source wire 16 may comprise a wide variety of different designs incorporating an elongate shaft 30 and a distally disposed radioactive source 32. Preferably, the source wire 16 comprises the design disclosed in U.S. Pat. No. 5,728,042 to Schwager, which is hereby incorporated by reference.

Refer now to FIG. 4 which illustrates the centering catheter 18 utilized in the system 10 illustrated in FIG. 1. Catheter 18 may comprise a wide variety of centering and non-centering catheter designs such as those disclosed in European Patent Application Publication No. 0 688 580 A1 to Verin et al., European Patent Application Publication No. 0 633 041 A1 to Popowski et al., International Patent Application Publication No. WO 96/14898 to Bradshaw et al., U.S. Pat. No. 5,855,546 to Hastings et al., and U.S. Pat. No. 5,910,101 to Andrews et al., which are hereby incorporated by reference. For purposes of illustration only, centering catheter 18 is illustrated as comprising the design of FIG. 3 in European Patent Application Publication No. 0 688 580 A1 to Verin et al.

Centering catheter 18 includes an elongate shaft 40 and a distally mounted balloon 42. The elongate shaft 40 includes an inflation lumen 44 to define a fluid path connecting the interior of the balloon to a proximally connected inflation device (not shown). The elongate shaft 40 also includes a source lumen 46 which is sized and adapted to receive the radioactive source wire 16 illustrated in FIG. 3. The distal end of the elongate shaft 40 includes a guide wire lumen 48 which is sized and adapted to receive the guide wire 12 illustrated in FIG. 2.

The balloon 42 includes a proximal waist 43, a distal waist 45, and a plurality of middle waists 47. The middle waists 47 may be defined by a belt 41 or may be molded into the balloon 42 during the manufacture thereof. Belt 41 may comprise a coil or band of polymeric or metallic material, preferably a radiopaque material. By providing a plurality of middle waists 47, the balloon 42 is able to easily conform to a curve to thereby maintain the source lumen 46 in the center of the vessel despite curvature thereof. By maintaining the source lumen 46 in the axial center of a vessel, the radioactive source 32 delivers a uniform dosage to the vascular wall.

Figure 5B:
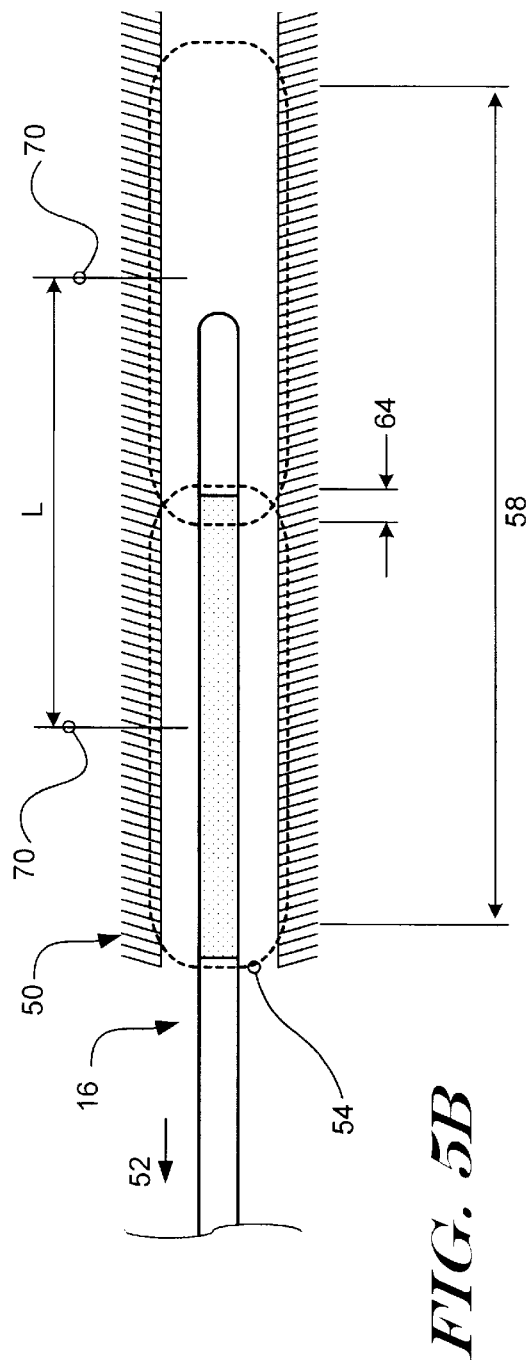

Refer now to FIG. 5A and 5B which illustrate the radiation source wire 16 disposed in the vasculature 50. FIG. 5A shows the radioactive source 32 in a first position, and FIG. 5B illustrates the radioactive source in a second position displaced from the first position by a distance L in the direction of arrow 52. The distance L illustrated in FIG. 5B corresponds to the distance L between the radiopaque markers 24 and 26 disposed on the guide wire 12 as shown in FIG. 2.

In the embodiment illustrated, the radioactive source 32 comprises a line source having a generally elliptical (uniform center with tapered ends) dose line 54. Due to the elliptical dose line 54, only a portion of the dose length 56 provides a full dose 58 to the vessel wall 50. The remainder of the dose length 56 provides a partial dose to the vessel wall 50 in the proximal dose fall-off (edge effect) region 60 and the distal dose fall-off (edge effect) region 62. Because vessel wall 50 corresponding to the proximal and distal dose fall-off regions 60 and 62 only receives part of the nominal or full dose, the present invention provides a means for overlapping the dose fall-off regions to provide a full dose in the overlap region 64 as illustrated in FIG. 5B.

This is accomplished by displacing the radioactive source 32 a distance L in the direction indicated by arrow 52 wherein the length L is equal to the distance between a proximal point 66 in the proximal dose fall-off region 60 and a distal point 68 in the distal dose fall-off region 62. The proximal point 66 and the distal point 68 preferably correspond to points on the dose line 54 equal to half (50%) of the nominal or full dose such that the total dose in the overlap region 64 is approximately equal to the nominal dose. By displacing the center line 70 (or other reference point) of the radioactive source 32 the distance L, the full dose region 58 (including overlap region 64) is distributed over substantially the entire treatment length.

Figure 6A:
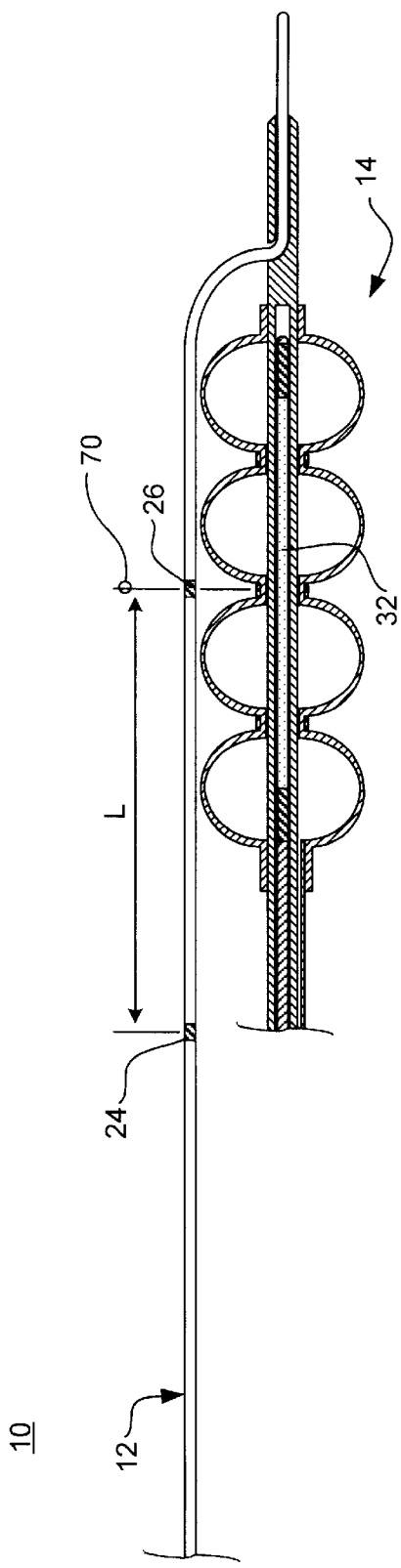
FIGS. 6A and 6B are partially cross-sectioned side views illustrating a method of administering ionizing radiation using the system illustrated in FIG. 1.
Figure 6B:
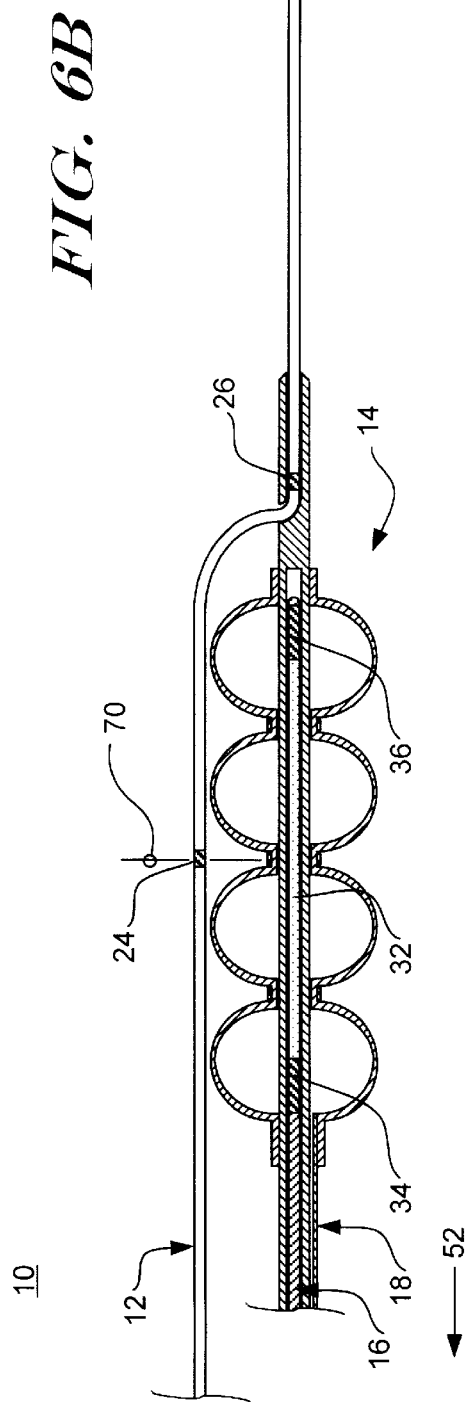

Refer now to FIGS. 6A and 6B which illustrate a method of administering ionizing radiation to a vessel wall using the system 10 illustrated in FIG. 1. For purposes of illustration and clarity only, the vessel walls are not shown in FIGS. 6A and 6B. It is to understood, however, that the system 10 is designed for use in the vascular system of a patient for purposes of administering ionizing radiation to inhibit or reduce the effects of restenosis. This method requires the use of elongate radiation device 14 and guide wire 16. As mentioned previously, the radiation device 14 may comprise any intravascular device having a distally disposed radioactive source. For purposes of illustration only, the method of the present invention is described with reference to a radiation device 14 that includes a centering catheter 18 and a source wire 16.

Initially, the guide wire 12 is inserted into the vasculature of the patient such that the proximal and distal radiopaque markers 24 and 36 are disposed adjacent the treatment site. As mentioned previously, more than two radiopaque markers 24 and 26 may be utilized, depending on the length of the treatment site and the length of the radiation source 32. For example, if a relatively short radiation source is utilized to treat a relatively long treatment site, it may be necessary to provide three, four, five or more radiopaque markers on the guide wire 12. Each of the radiopaque markers would be disposed on the distal portion of the guide wire 12 and separated by a distance L. The repositioning steps described below would be repeated for each radiopaque marker.

After the guide wire is positioned within the vasculature such that the radiopaque markers 24 and 26 are adjacent the treatment site, the radiation device 14 may be advanced over the guide wire 12 or alongside the guide wire 12, depending on whether or not the radiation device 14 incorporated a guide wire lumen. If the radiation device 14 includes a source wire 16 and a centering catheter 18, the centering catheter 18 may be advanced prior to advancing the source wire 16. The centering catheter 18 may be advanced manually in a conventional manner with the assistance of x-ray fluoroscopy, and the source wire 16 may be advanced into the centering catheter manually or utilizing an afterloader.

The radiation device 14 is advanced through the vasculature until the radiation source 32 is disposed adjacent to, and in alignment with, the radiopaque distal marker 26. This may be accomplished by centering the proximal and distal radiopaque markers 34 and 36 of the source wire 16 on either side of the proximal marker 24 of the guide wire 12. Alternatively, the center belt 41 may be aligned with the radiopaque marker 24 of the guide wire 12, and the radiopaque markers 34 and 36 of the source wire 16 may be aligned with the center belt 41. Regardless of the method, x-ray fluoroscopy is utilized to effectively align the center line 70 of the radioactive source 32 with the distal marker 26. Those skilled in the art will recognize that other suitable reference lines and arrangements of radiopaque markers may be utilized to accomplish the same result.

After exposing the treatment site with the radioactive source 32 positioned adjacent to the distal marker 26 for the desired period of time, the radioactive device 14 is displaced in the direction indicated by arrow 52 the distance L such that the center line 70 of the radioactive source 32 is in alignment with the proximal marker 24. By so positioning the radioactive source 32, dose overlap is created as discussed with reference to FIGS. 5A and 5B. After the desired period of time, the radiation device 14 may be withdrawn, or displaced in the direction indicated by arrow 52 the distance L such that the radiation source 32 is adjacent yet another radiopaque marker (not shown) disposed on the guide wire 12. Those skilled in the art will recognize that the radioactive source 32 may be repositioned in the proximal direction as described, or in the distal direction if desired.

From the foregoing, it should be apparent to those skilled in the art that the present invention provides a system 10 for intravascular ionizing radiation therapy including a radiation device 14 and a guide wire 12. The guide wire 12 incorporates two or more radiopaque markers 24 and 26 to facilitate precise repositioning of the radiation source 32 along the length of the treatment site. The radiopaque markers 24 and 26 are separated by a distance L, which may be different than (e.g., slightly less than) the length of the radioactive source 32. This produces partial dose overlap 64 when the radioactive source is positioned sequentially adjacent each radiopaque marker 24 and 26 on the guide wire 12. This provides more uniform and complete radiation exposure along the length of the treatment site.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A medical system for intravascular ionizing radiation therapy, comprising:

an elongate radiation device having a radiopaque marker and a radioactive source disposed adjacent a distal end thereof, the radioactive source having a length and a dose distribution, the dose distribution having a nominal dose, a proximal dose fall-off, a distal dose fall-off, a proximal point in the proximal dose fall-off corresponding to 50% of the nominal dose, a distal point in the distal dose fall-off corresponding to 50% of the nominal dose, wherein the proximal 50% point is separated from the distal 50% point by a distance L; and an elongate guide wire having a plurality of radiopaque markers disposed adjacent a distal region thereof, the radiopaque markers separated by the distance L such that dose fall-off overlap is created when the radioactive source is positioned adjacent each radiopaque marker.

2. A medical system as in claim 1, wherein the distance L is less than the length of the radioactive source.

3. A medical system as in claim 1, wherein the radioactive source is a line source.

4. A medical system as in claim 1, wherein the elongate radiation device includes a delivery catheter and a source wire insertable therein, the radioactive source disposed adjacent a distal end of the source wire.

5. A medical system as in claim 4, wherein the delivery catheter includes a guide wire lumen, and wherein the guide wire is disposed in the guide wire lumen.

6. A medical system as in claim 5, wherein the delivery catheter includes a centering means disposed adjacent a distal end thereof.

7. A medical system as in claim 6, wherein the delivery catheter includes a radiopaque marker disposed adjacent the centering means.

8. A medical system as in claim 7, wherein the centering means has a proximal end, a distal end and a midpoint therebetween, and wherein the radiopaque marker is disposed adjacent the midpoint of the centering means.

9. A medical system as in claim 7, wherein the centering means has a proximal end, a distal end and a midpoint therebetween, and wherein the radiopaque marker is disposed adjacent the proximal end of the centering means.

10. A medical system as in claim 7, wherein the centering means has a proximal end, a distal end and a midpoint therebetween, and wherein the radiopaque marker is disposed adjacent the distal end of the centering means.

11. A medical system as in claim 10, wherein the delivery catheter includes a first and second radiopaque marker, the first radiopaque marker disposed adjacent the proximal end of the centering means and the second radiopaque marker disposed adjacent the distal end of the centering means.

12. A medical system as in claim 10, wherein the source wire includes a radiopaque marker disposed adjacent the radioactive source.

13. A guide wire for use in combination with an elongate radiation device for intravascular ionizing radiation therapy, wherein the elongate radiation device includes a radioactive source disposed adjacent a distal end thereof, the radioactive source having a length and a dose distribution, the dose distribution having a nominal dose, a proximal dose fall-off, a distal dose fall-off, a proximal point in the proximal dose fall-off corresponding to 50% of the nominal dose, a distal point in the distal dose fall-off corresponding to 50% of the nominal dose, wherein the proximal 50% point is separated from the distal 50% point by a distance L, the guide wire comprising:

an elongate shaft having a distal region; and two or more radiopaque markers disposed adjacent the distal region of the shaft, the radiopaque markers separated by the distance L such that dose fall-off overlap is created when the radioactive source is positioned adjacent each radiopaque marker.

14. A guide wire as in claim 13, wherein the distance L is less than the length of the radioactive source.

15. A method of administering ionizing radiation at a treatment site within a patient's vasculature, comprising the steps of:

providing an elongate radiation device having a radiopaque marker and a radioactive source disposed adjacent a distal end thereof, the radioactive source having a length and a dose distribution, the dose distribution having a nominal dose, a proximal dose fall-off, a distal dose fall-off, a proximal point in the proximal dose fall-off corresponding to 50% of the nominal dose, a distal point in the distal dose fall-off corresponding to 50% of the nominal dose, wherein the proximal 50% point is separated from the distal 50% point by a distance L;

providing an elongate guide wire having a proximal and a distal radiopaque marker disposed adjacent a distal region thereof, the radiopaque markers separated by the distance L;

inserting the guide wire into the vasculature of the patient;

advancing the guide wire through the vasculature until the radiopaque markers are disposed adjacent the treatment site;

inserting the radiation device into the vasculature of the patient;

positioning the radioactive source adjacent one of the radiopaque markers; and repositioning the radioactive source adjacent the other of the radiopaque markers such that dose fall-off overlap is created.

16. A method as in claim 15, wherein the radiation device is inserted into the vasculature over the guide wire.

17. A method as in claim 15, wherein the distance L is less than the length of the radioactive source.

* * * * *